United States Patent [19]

Warnecke

[11] 4,456,011

[45] Jun. 26, 1984

[54] BALLOON-CATHETER

[76] Inventor: Irene Warnecke, Heerstrasse 11, 1000 Berlin 19, Fed. Rep. of Germany

[21] Appl. No.: 332,929

[22] Filed: Dec. 21, 1981

[30] Foreign Application Priority Data

Dec. 22, 1980 [DE] Fed. Rep. of Germany ....... 3048923

[51] Int. Cl.³ .......................................... A61M 25/00
[52] U.S. Cl. .................................... 128/325; 604/101
[58] Field of Search ...................... 604/96, 97, 98, 99, 604/100, 101; 128/344, 656, 658

[56] References Cited

U.S. PATENT DOCUMENTS 4,130,119 12/1978 Sessions et al. ..................... 128/325
4,338,942 7/1982 Fogarty ............................... 128/325
4,341,218 7/1982 Ü604 ......................................... 97
4,346,712 8/1982 Honda et al. ......................... 604/99
4,364,392 12/1982 Strother et al. ..................... 128/325

*Primary Examiner*—Kyle L. Howell
*Assistant Examiner*—George Yanulis
*Attorney, Agent, or Firm*—Ralf H. Siegemund

[57] ABSTRACT

A catheter for intravascular occlusion of vascular connections and other defects provided with a tubular element and carrying at its very end a position-balloon behind which is provided the occlusion-balloon; the latter is detachable from the catheter and the position-balloon is either attached to the catheter or to the occlusion balloon to be detached therewith.

12 Claims, 2 Drawing Figures

BALLOON-CATHETER

This invention relates to balloon-catheters and, in particular, to such occlusion-catheters for use in blood vessels and in the heart as therapeutic tools, according to the preamble of claim 1. A catheter of this type has been described in the German DE-OS (laid open print) No. 2817 972.

It is already known in the art that large vessels such as the inferior vena cava (Hunter, J. A. et al.: Annals of Surgery, Vol. 171, Nr. 2, page 315, 1970) and also small vessels as in the brain (Serbinenko, F. A.: J. Neurosurg., Vol. 41, page 125, 1974) can be occluded by a catheter device specified by a detachable balloon at the tip of the catheter to be filled with fluid or hardening material.

The structure of the catheter that can be used in this way has been disclosed, e.g., in the FR-A No. 23 83 673.

Also a large vascular connection, for instance between the aorta and the pulmonary artery, such as the persistent ductus arteriosus, can be occluded by means of a different catheter device used by W. Porstmann et al. (Thoraxchirurgie, Vol. 15, page 199, 1967), wherein a plug made of foamed material could be grafted with the aid of an aortic-venous guide wire. This method, however, is technically complicated, time and radiation consuming and risky to the patient because of potential damages to the arteries used and potential thrombosis. Furthermore a dislodgement of the foamed plug occurs due to a lack in exact positioning and inadequate matching with respect to the vascular connection to be occluded.

On the other hand, catheters with umbrella-type occluding members are already known in the art (FR-A No. 23 28 483, GB-PS No. 15 09 023) and have been used for the same purpose. As they are rigid, it seems hazarduous to push them is necessary in cardiac catherization. The main disadvantage of this device is due to the fact that the umbrella will be attached with grappling hooks in the tissue causing damage to it.

All these procedures and/or catheter devices are actually not being used as a matter of routine on account of the mentioned drawbacks.

Especially in the first-mentioned type of catheter which is provided with a detachable balloon, it will be readily observed that we are practically faced with almost impossible to resolve position problems as to place the balloon in the vascular connection to be occluded.

For this reason it is the object of this invention to provide for a catheter, and particularly a cardiac catheter with which vascular connections can be occluded by means of an occluding body or member, that can be precisely positioned. The catheter may be constructed such that it can be introduced from a peripheral vessel, preferably a vein, and that it allows within a broad range an adaptation or matching to the defect to be occluded.

This aim is achieved in accordance with the invention by way of the features disclosed in the claims.

The advantages achieved in the application of this invention are comprised in particular in that it is possible with a catheter of this invention to precisely place a detachable occlusion member in the vascular connection or in cardiac septum defects by means of the distal position-balloon.

The occlusion member or plug is to be made to adjust to the shape and size of the vascular connection to be occluded or to the cardiac septum defect to be closed. Moreover, it is possible for the occlusion member to be manufactured of a material and to be structured with a surface such that said member is not only biocompatible but will also be enclosed and shortly fixed by new growth of endogenic fibrous tissue. As a consequence a late reopening of the connection due to phagocytosis of the material is excluded. The occlusion member is mounted on the catheter in such a manner that it will adhere initially, whereas it can be detached at a predetermined point in time. The release from the catheter may be carried out without tension or pulling on the occlusion plug by using an outer cannula as a sheath. The injection of the filling material for the occlusion member is effected simultaneously with de-airing. Furthermore, it is possible to measure the inflation or filling pressures and to recognize an adequate filling of the occlusion balloon also by radiologic means using radiopaque filling substances. The filling substances may be suctioned off the balloon at a predetermined temporal interval before setting or curing takes place, and the catheter with evacuated occlusion-balloon may be removed from the body if so required. Additional passages or channels in the plurilumina catheter may be significant for diagnostic purposes as measuring oxygen and blood pressures.

Summarily, the catheter described is distinctive in that it can be used like a diagnostic cardiac catheter in the vascular system and in the heart. It may be of such minute size that it can be applied not only in adults but also in children and babies. Particularly it permits the occlusion of one of the most frequent lesions in congenital heart disease, the persistent ductus arteriosus, by approach via a vein whereby a damage of a peripheral artery is prevented.

An embodiment according to the invention provides for the position-balloon to be also detachable from the catheter. This embodiment is distinctive and characterized by a simpler method of manufacture, which also facilitates the release and detachment of the catheter, as the position-balloon is not withdrawn through the occlusion-balloon. Both balloons or balloon-sections are detachable from the catheter. The position-balloon is constructed such way that when it remains in the body it is not adversely affecting the blood stream, or the position-balloon will be withdrawn from the tip of the catheter into the opening of the occlusion-balloon and there detaches itself.

The foregoing objects and advantages of the invention will become more apparent as the following detailed description is read in conjunction with the accompanying schematic drawings, which respectively are longitudinal sections of two embodiments of this invention.

Figure 1:
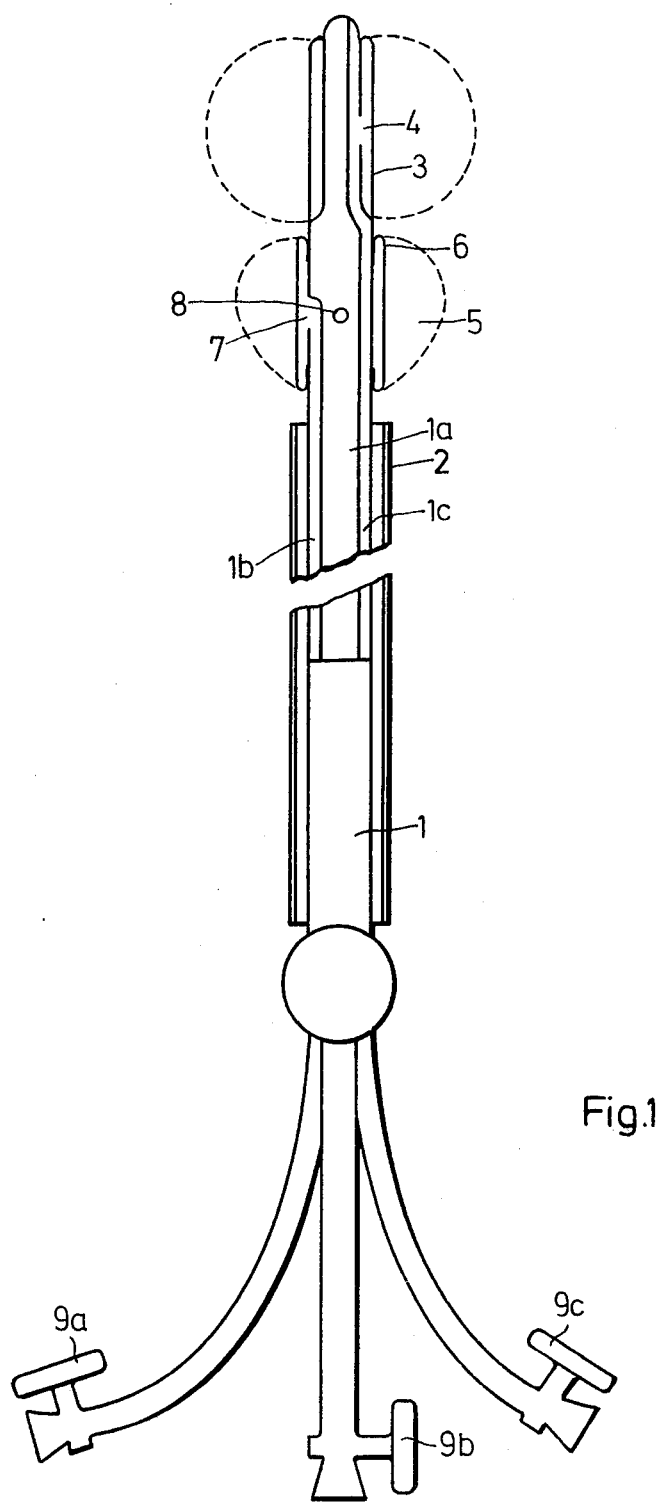
FIG. 1 shows a balloon catheter partially in section in accordance with the preferred embodiment of the invention.

Referring to the drawing in FIG. 1 shown therein and generally designated by the reference character 1 is a catheter that comprises three passages 1a–c. At the distal end thereof the so-called position-balloon 3 is fixedly attached to the catheter. This position-balloon can be expanded via an opening 4 communicating with passage 1 c. At a predetermined distance from this position-balloon 3— which distance is among others a function of the type of connection to be occluded - a second balloon, the so called occlusion-balloon 5 is mounted. The occlusion-balloon 5 is releasably attached to the catheter such as e.g. by applying an adhesive which will dissolve chemically or in a thermic reaction which requires a certain period of time or, as in the example illustrated, by means of an elastic tube 6. Such a piece of tubing made of silicone-rubber may readily be connected during manufacture to the catheter before mounting the occlusion-balloon 5. This has the advantage that under the prevailing pressure conditions a tight seal is assured over the length of the occlusion-balloon 5. It is likewise possible to use elastic rings as seal. The occlusion-balloon 5 can be evacuated through an opening 7 in the passage 1 b of the catheter. Expanding and/or filling Of the occlusion-balloon 5 with liquid silicone-rubber is effected via passage 1 a and opening 8. Shown in the drawing are also the opening- and closing-cocks 9 a–c for the passages 1 a–c, respectively. The functions of the catheter and its mode of operation, and in particular the operation of the sheath 2, being displaceable on the catheter will be explained hereinafter.

The catheter described is introduced through the leg vein and pushed via the inferior vena cava to the right heart and from the pulmory artery through the persistent ductus arteriosus to the aorta, like routinely done in diagnostic heart catherization for this lesion. The position-balloon 3 is now filled with gas or dye via passage 1 c, the catheter is withdrawn until the position-balloon 3 stops at the insertion of the persistent ductus arteriosus. In that position the occlusion-balloon 5 is determined to lie in the vascular connection to be occluded. Subsequently, the occlusion-balloon 5 will be filled with liquid radiopaque silicone-rubber via passage 1 a, which passage is at the same time de-aired via passage 1 b. Hereafter the position-balloon 3 is deflated via passage 1 c. After the silicone-rubber within the occlusion-balloon 5 has hardened the sheath 2 is advanced on the catheter up to the occlusion plug. Then the catheter is withdrawn through the sheath without tension on the occlusio plug. Catheter and sheath 2 are removed from the body, the occlusion plug remains to close the vascular connection.

As pointed out above, the occlusion-balloon 5 is filled with a radiopaque, liquid material impenmeable to radiation and being compatible with the material of the balloon itself and also biocompatible. While the material stays liquid during the filling procedure, it must set after a certain lapse of time. As examples for such amsubstance we cite but silicone oil and hardener.

Furthermore, the catheter may also be provided with additional passages or lumina for specific purposes such as e.g. for measuring the blood pressure or for taking blood samples or, likewise, for measuring the blood oxygen or injecting substances such as contrast medium into the blood stream.

Figure 2:
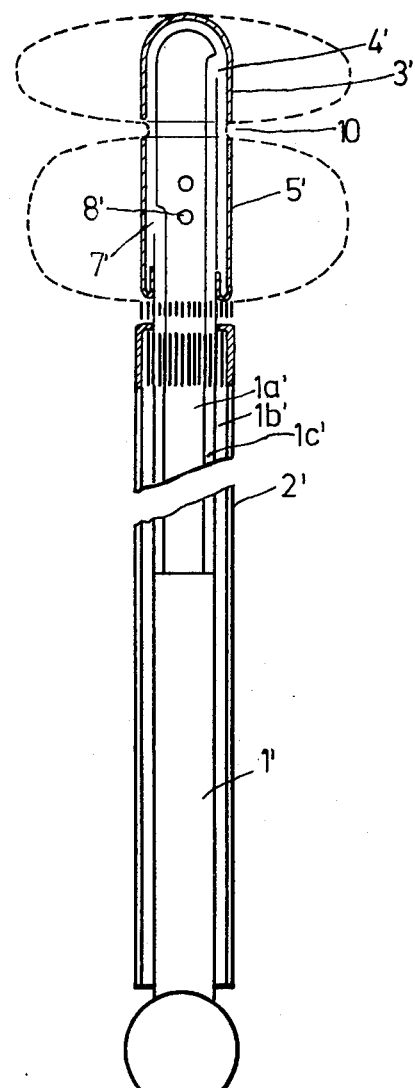
FIG. 2 is a similar view of a modified construction for a balloon catheter.

Referring now to the drawing of FIG. 2, shown therein and generally designated by reference character 1' is a catheter that comprises three passages 1 a'–c' and the corresponding openings 4', 7', 8'. At the distal end of the catheter there is provided in this embodiment a balloon extending along a determined axial length of the catheter tip and sourrounding the terminal end. This balloon is divided into two spherical section via an annular member or ring 10, on account of its being preformed in this manner. The two balloon-sections correspond respectively to the position-balloon and the occlusion-balloon of FIG. 1. However, the two balloons are combined here in a common balloon having sections 3' and 5' and having been slipped onto the catheter and is releasably attached thereto such as by means of suitable adhesives or mechanical connections. Detachment of the balloon from the catheter is effected with the aid of the sheath 2'.

The catheter described is introduced through the leg vein, pushed via the inferior vena cava to the right heart and from the pulmonary artery through the persistent ductus arteriosus to the aorta, as is routinely done in diagnostic heart catherization for this lesion. The position-balloon 3' is filled with gas or dye via passage 1 c' and opening 4', then the catheter is withdrawn until the position-balloon 3' stops at the insertion of the persistent ductus arteriosus. In that position the occlusion-balloon 5' is determined to lie within the vascular connection to be occluded. In the same manner as described for the first embodiment, the occlusion-balloon 5' is filled with radiopaque, hardening silicone-rubber after previous de-airing. The respective passages and openings have been designated by reference characters 1a', 1b' and 7' and 8', respectively. The position-balloon 3' is deflated. When releasing the balloon sections 3', 5' from the catheter with the aid of the sheath 2' the evacuated position-balloon 3' is also withdrawn with the tip of the catheter—where it has been releasably fixed—into the catheter channel of the occlusion balloon 5', and this until such time as the continued withdrawal of the catheter will result in a release from the tip.

Catheter and sheath are removed from the body, the occlusion plug remains exactly positioned and completely occludes the persistent ductus arteriosus.

The embodiments of the invention in which an exclusive property or privilege is claimed are defined as follows:

1. A balloon-catheter with a detachable occlusion member for intravascular and permanent occlusion of vascular connections and cardiac septal defects, the improvement, comprising, a position balloon disposed at the distal end of the catheter the position-balloon being connected to the catheter; an occlusion-balloon detachably mounted on the catheter at a particular distance from the position balloon and rearwardly displaced from the distal end in a direction toward the other end of the catheter; and means for providing for filling and emptying of the balloons so that they can be separately filled and evacuated via separate lumina from the other end of the catheter.

2. A balloon-catheter according to claim 1, wherein the position-balloon is fixedly attached to the catheter, while the detachable occlusion-balloon can be released by effecting a relative displacement across the evacuated position-balloon.

3. A balloon-catheter according to claim 1, wherein the position-balloon is detachably mounted to the catheter.

4. A catheter according to one of the claims 1, wherein the occlusion-balloon is made of a biocompatible, elastic and thin material, which in the evaucated state lies snug with the catheter.

5. A catheter according to claim 4, wherein the occlusion-balloon is made of silicone-rubber.

6. A catheter according to claim 4, wherein the occlusion-balloon is made of polyurethane.

7. A catheter according to claim 4, wherein the surface of the occlusion-balloon is provided with additional pieces of material for enhancing adhesive action between the occlusion-balloon and adjoining tissue.

8. A catheter to one of the claims 1, wherein the occlusion balloon is detachably held on the catheter by means of elastic tubing.

9. A catheter according to one of the claims 1, wherein an additional passage is provided, communicating likewise with the occlusion-balloon through an opening.

10. A catheter according to claims 1, wherein the occlusion-balloon is detachable with the aid of a sheath displaceably mounted on the catheter.

11. A balloon-catheter according to claim 3, wherein the position-balloon and the occlusion-balloon are constructed as a single balloon, there being an annular member provided as partition and being located at a defined distance from the terminal end of the catheter and lying snug with the catheter.

12. A balloon-catheter according to claim 11, wherein the position-balloon and a tip of the catheter are releasably attached to each other.

* * * * *